(12) United States Patent
Elsener et al.

(10) Patent No.: US 9,297,728 B2
(45) Date of Patent: *Mar. 29, 2016

(54) STORAGE UNIT AND TRANSFER SYSTEM FOR BIOLOGICAL SAMPLES

(75) Inventors: Donat Elsener, Thun (CH); Dietmar Reisch, Thun (CH)

(73) Assignee: Brooks Automation, Inc., Chelmsford, MA (US)

( * ) Notice: Subject to any disclaimer, the term of this patent is extended or adjusted under 35 U.S.C. 154(b) by 179 days.

This patent is subject to a terminal disclaimer.

(21) Appl. No.: 12/941,009

(22) Filed: Nov. 5, 2010

(65) Prior Publication Data

US 2011/0121001 A1    May 26, 2011

Related U.S. Application Data

(63) Continuation of application No. 11/680,045, filed on Feb. 28, 2007, now Pat. No. 7,829,028.

(30) Foreign Application Priority Data

Mar. 2, 2006 (CH) .................................. 0334/06

(51) Int. Cl.
*B01L 3/00* (2006.01)
*B65D 85/48* (2006.01)
*B65D 1/24* (2006.01)
(Continued)

(52) U.S. Cl.
CPC . *G01N 1/312* (2013.01); *B01L 9/52* (2013.01); *A61B 10/0096* (2013.01); *B01L 2200/04* (2013.01); *B01L 2300/0822* (2013.01);
(Continued)

(58) Field of Classification Search
USPC .................. 422/104, 536, 559, 561; 222/500, 222/528–9; 206/456
See application file for complete search history.

(56) References Cited

U.S. PATENT DOCUMENTS 4,236,635 A * 12/1980 Namiki .......................... 206/456
4,971,199 A * 11/1990 Price et al. ................ 206/387.15
(Continued)

FOREIGN PATENT DOCUMENTS

DE        2753223       6/1978
DE        4306310       9/1994
(Continued)

OTHER PUBLICATIONS

MJ. Schermer; "confocal scanning microscopy . . ."; cited in application; Feb. 28, 2007.

*Primary Examiner* — Lyle Alexander
*Assistant Examiner* — Jennifer Wecker
(74) *Attorney, Agent, or Firm* — Perman & Green, LLP; Colin C. Durham (57) ABSTRACT

A storage unit for biological samples has a horizontal footprint and multiple storage compartments separated by partitions and enclosed by a frame. The storage compartments have first and second openings and are fitted to the shape of a biopsy cassette or a glass slide and have a retention mechanism preventing the substantially vertical cassettes or slides in the storage compartments from falling out through the first opening and/or the second opening. A transfer system allows at least two storage units or at least one storage unit and one collection unit to be situated one above the other in alignment and displaced in relation to one another. The transfer system has a manipulator by which a biopsy cassette or a glass slide may be pushed from one storage unit to another, or into the collection unit.

27 Claims, 3 Drawing Sheets

US 9,297,728 B2
Page 2

(51) Int. Cl.
  B01L 9/00 (2006.01)
  B65D 1/36 (2006.01)
  B65D 25/04 (2006.01)
  G01N 1/31 (2006.01)
  *A61B 10/00* (2006.01)
  *B67D 3/00* (2006.01)
  *B65D 85/804* (2006.01)
  *B65D 85/14* (2006.01)
  *G01N 21/00* (2006.01)
  *G02B 21/34* (2006.01)
  *G03B 21/64* (2006.01)
  *G01N 35/00* (2006.01)

(52) U.S. Cl.
  CPC ...... *G01N2035/00089* (2013.01); *G02B 21/34* (2013.01); *G03B 21/64* (2013.01)

(56) References Cited

U.S. PATENT DOCUMENTS

| | | |
|---|---|---|
| 5,665,398 A | 9/1997 | McCormick |
| 5,690,892 A | 11/1997 | Babler et al. |
| 5,968,436 A | 10/1999 | Takezaki |
| 6,004,512 A | 12/1999 | Titcomb et al. |
| 6,305,543 B1 * | 10/2001 | Lafond et al. ............... 206/456 |
| 6,395,536 B2 | 5/2002 | Freeman |
| 6,827,907 B2 | 12/2004 | Fattinger et al. |
| 6,847,481 B1 | 1/2005 | Ludl et al. |
| 7,407,630 B2 | 8/2008 | Reed et al. |
| 2001/0003652 A1 | 6/2001 | Freeman |
| 2002/0108915 A1 * | 8/2002 | Stitt ......................... 211/41.12 |
| 2002/0197139 A1 | 12/2002 | Chinbe et al. |
| 2003/0138353 A1 * | 7/2003 | Bargoot et al. ............... 422/58 |
| 2004/0013576 A1 * | 1/2004 | Gfrorer et al. ............... 422/104 |
| 2004/0251796 A1 | 12/2004 | Wood |
| 2006/0072988 A1 | 4/2006 | Hariki et al. |
| 2007/0278120 A1 | 12/2007 | Ho Fung et al. |

FOREIGN PATENT DOCUMENTS

| | | |
|---|---|---|
| DE | 29712535 | 9/1997 |
| EP | 0611598 | 8/1994 |
| EP | 0904841 | 3/1999 |
| EP | 1148372 | 10/2001 |
| GB | 1593064 | 11/1977 |
| WO | WO 9423326 A1 * | 10/1994 |

* cited by examiner

STORAGE UNIT AND TRANSFER SYSTEM FOR BIOLOGICAL SAMPLES

RELATED APPLICATIONS

The present application is a continuation of U.S. application Ser. No. 11/680,045, filed Feb. 28, 2007, which claims priority of Swiss patent Application No. CH 0334/06, filed on Mar. 2, 2006, of which the entire disclosure is herein incorporated by explicit reference for all intents and purposes.

FIELD OF THE INVENTION

The present invention relates to a storage unit for storing large numbers of biological samples that are fixed on a sample cassette or slide, and more particularly to an automated system for storing and transferring sample cassettes or slides on which biological samples are fixed.

BACKGROUND

In biological laboratories, in particular in the laboratories of pathological institutes of universities or hospitals, biological samples, e.g., tissue samples obtained by biopsy, are very often stored as tissue pieces in cassettes or as thin sections on glass slides. A selection of such cassettes and glass slides is offered, for example, by THERMO SHANDON. These cassettes typically comprise a flat, cuboid sample cage having vertical closed lateral walls and a lower support surface pierced in a lattice. The upper storage surface is typically provided by a hinged cover having a snap closure, which is connected via a joint to the sample cage and is also pierced in a lattice. These samples are normally embedded, in paraffin, for example (see, for example, U.S. Pat. No. 5,665,398, U.S. Pat. No. 5,968,436, or DE 43 06 310 A1) and stored at room temperature, in the refrigerator (at approximately +4° C.), in the deep freeze (at approximately −18° C.), at lower temperature in an environment of solid $CO_2$ (at approximately −80° C.), or at extremely low temperature in liquid nitrogen (at approximately −196° C.). A very large number of such samples, which may reach the hundreds of thousands, if not the millions, complicates finding a specific sample. This finding becomes more and more difficult with decreasing storage temperature. The targeted removal of precisely one single sample from a liquid nitrogen container is typically not possible. Normally, a container that contains many samples must be drawn from the nitrogen tank so that the desired sample may be selected. This is a time-consuming process in which the integrity and quality of the other samples which are not selected is also put into play to a greater or lesser degree.

The joint storage of samples typically does not represent a problem for the questions of pathology, contamination of neighboring samples by "carryover" may generally be neglected. A selection of containers for storing and providing such cassettes and glass slides (in particular at room temperature, see also EP 1 148 372 A2) is also offered by THERMO SHANDON. Laboratories of universities and the pharmaceutical industry, which are concerned with protein studies on or in frozen samples, have entirely different requirements in this context.

In pharmaceutical research, chemical or biochemical compounds are routinely tested for their potential pharmaceutical activity. For this purpose, a large number of samples must be provided within a very brief time. In laboratories of pharmaceutical research, microtubes are therefore used, which contain a sufficient quantity of a specific substance. In order to be able to handle the enormous numbers of such microtubes as economically as possible, they are packed in "microtube cluster racks". For robotic handling, those racks, which have a footprint corresponding to the footprint of a microplate according to the SBS standard (SBS=standard for biomolecular screening), which is thus often referred to as the "SBS footprint", are especially preferred. In the meantime, this standard has been normalized by ANSI (American National Standards Institute) as ANSI/SBS 1-2004. Microtube cluster racks having 96 or 384 microtubes are known, for example, under the trade name REMP® Tube Technology™.

Thin sections of fixed samples, embedded in paraffin, for example, are routinely applied to glass slides and evaluated using light microscopy in pathology. Following Table 1 gives an overview of the most common glass slides and dimensions:

TABLE 1

| | Type | Inch: 1 × inches | Metric: 25 × 75 mm |
|---|---|---|---|
| Dimensions | Length × width (tolerances) | 76.2 mm × 25.4 mm (±0.5 mm) | 75 mm × 25 mm (±0.5 mm) |
| Thickness | "standard" | 1.02 mm (±0.05 mm) | 1.02 mm (±0.05 mm) |
| | "thick" | 1.2 mm (±0.1 mm) | |
| Handling | corners | sharp, beveled | sharp, rounded |
| | edges | sharp, beveled | sharp |
| | surfaces | blank, sandblasted, painted on one or both sides | blank, sandblasted, painted on one or both sides |

(Table according to: Schermer, M. J.: Confocal scanning microscopy in microarray detection, in "DNA Microarrays, A practical approach"; Mark Schena (ed.), Oxford University Press 1999, 17-42)

The current applicant distributes microtube cluster racks having 96 or 384 microtubes under the trade name REMP® Tube Technology™. These differ from the racks and microtubes from the other prior art substantially in that the sample tubes are provided by situating at least two racks one on top of another and sample tubes are pushed from the upper rack using a manipulator into correspondingly positioned receptacle cavities of the lower rack. Vice versa, this transfer process may also be performed by pushing sample tubes using a manipulator from the lower rack into correspondingly positioned receptacle cavities of the upper rack (see, for example, EP 0 904 841 B1 or U.S. Pat. No. 6,827,907 B2).

BRIEF SUMMARY OF THE INVENTION

It is an object of the present invention is to suggest an alternative storage unit—in relation to the one cited at the beginning—for storing and providing a large number of biological samples.

The aforementioned object is achieved by the features of the claims in that a storage unit for biological samples having a substantially horizontal main footprint and multiple storage compartments is suggested. These storage compartments are at least partially separated from one another by partitions and enclosed by a peripheral frame. The partitions and the peripheral frame are situated substantially perpendicular to the main footprint. In addition, the storage compartments have both a first opening and also a second opening. The storage unit for biological samples according to the present invention is characterized in that the storage compartments are fitted to the shape of a biopsy cassette or to the shape of a glass slide and comprise retention means, which prevent the biopsy cassettes or glass slides, which are inserted through the first opening and/or the second opening into the storage compartments and stand substantially vertically, from falling out through the first opening and/or the second opening.

Advantages of the storage unit for biological samples according to the present invention comprise:

The biopsy cassettes or glass slides having the biological samples may be inserted into the storage compartments robotically.

The biopsy cassettes or glass slides having the biological samples may be removed from the storage compartments robotically.

The biopsy cassettes or glass slides having the biological samples may be repositioned from one storage compartment to another storage compartment of the same storage unit robotically.

The biopsy cassettes or glass slides having the biological samples may be repositioned from one storage compartment to another storage compartment of another storage unit robotically.

Each biopsy cassette and each glass slide having the biological samples contained therein or thereon may be addressed individually and stored and provided robotically without any influence on other samples.

The robotic storage and provision of the biopsy cassettes and glass slides having the biological samples contained therein or thereon may be performed at practically any arbitrary temperature.

BRIEF DESCRIPTION OF THE DRAWINGS

Exemplary embodiments of the storage unit according to the present invention will now be explained in greater detail on the basis of schematic figures of the drawing, which do not restrict the scope of the present invention, wherein:

FIG. 5 shows views of a closed biopsy cassette known per se from the prior art, wherein

DETAILED DESCRIPTION OF THE INVENTION

Figure 1:
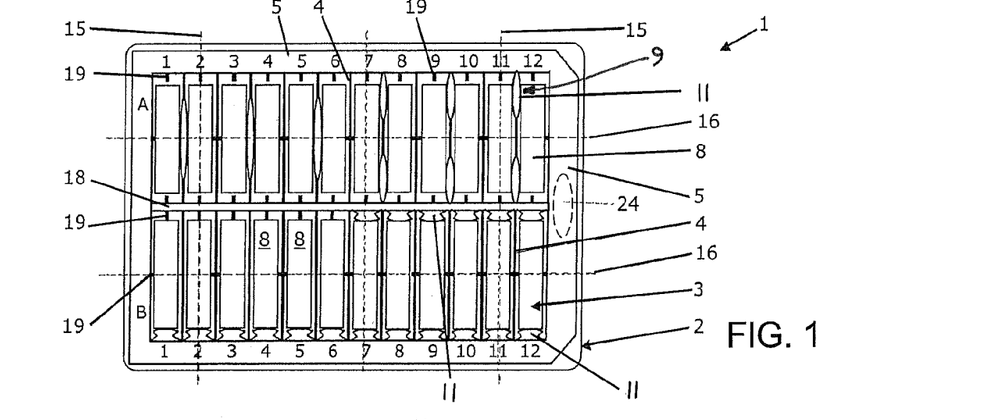
FIG. 1 shows a top view of a storage unit suitable for biopsy cassettes, in which the substantially vertically standing biopsy cassettes are packed tightly and situated transversely.
Figures 5A, 5B, 5C, 6, 7:
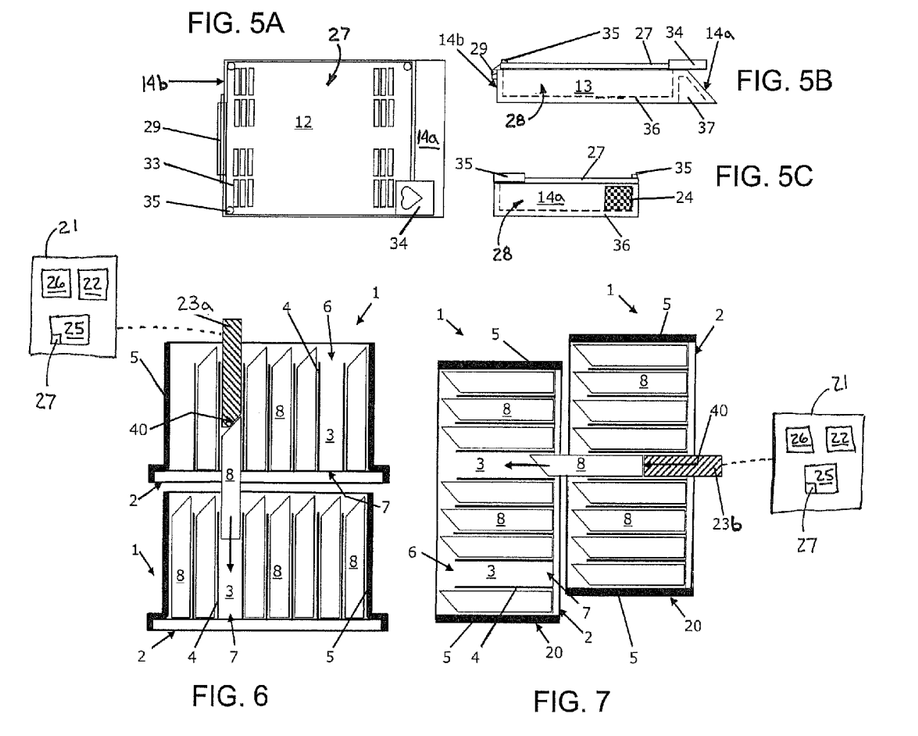
FIG. 5A shows a top view of the support surface of the cover of the biopsy cassette.
FIG. 5B shows a view of a vertical surface of the cage of the biopsy cassette.
FIG. 5C shows a view of the forward face of the cage of the biopsy cassette.
FIG. 6 shows a vertical section through two storage units situated one above the other in alignment having the SBS standard footprint of a standard microplate, a biopsy cassette being pushed vertically from the upper storage unit into the lower storage unit.
FIG. 7 shows a vertical section through two storage units situated one above the other in alignment, a biopsy cassette being pushed horizontally from the lower storage unit into the upper storage unit.

FIG. 1 shows a storage unit 1 for biological samples, having a main footprint 2 and multiple storage compartments 3, which are at least partially separated from one another by partitions 4 and are enclosed by a peripheral frame 5, the partitions 4 and the peripheral frame 5 being situated substantially perpendicular to the main footprint 2, and its storage compartments 3 having a first opening 6 and also a second opening 7 (see FIGS. 6 and 7). The storage compartments 3 have the same, substantially rectangular cross-sectional profile over their entire height in the storage unit 1 here. The storage compartments 3 are fitted to the shape of a biopsy cassette 8, which is inserted either through the first opening 6 or the second opening 7 into these storage compartments 3 standing substantially vertically and stands on one of its faces 14a, 14b (see, for example, FIG. 5C). The storage compartments 3 additionally comprise retention means 9, which are implemented here as single-sided and double-sided cushions 11. The retention means 9 run substantially perpendicular in relation to the main footprint 2 and are implemented to engage by way of a frictional force against the support surfaces 12 (see, for example, FIG. 5A) or on the vertical surfaces 13 (see, for example, FIG. 5B) of a biopsy cassette 8 inserted into a storage compartment 3. Due to this frictional force, these substantially vertically inserted biopsy cassettes 8 are prevented from falling out through the first opening 6 and/or the second opening 7 (no matter which side the storage unit 1 is tilted toward).

According to a first embodiment, the cushions 11 are implemented as double-sided, as shown in the storage compartments A1 through A12, referring to the row/column coordinates illustrated in FIG. 1. In connection with the present invention, "double-sided" is to be understood to mean "acting in two directions against the biopsy cassettes which press against them". These cushions 11 are implemented to engage using frictional force on the support surfaces 12 of a biopsy cassette 8 inserted into a storage compartment 3 and are situated on a longitudinal axis 16 (see storage compartments A1 through A6) running centrally and transversely to these storage compartments 3. The double-sided cushions 11 of a row of storage compartments (see A7 through A12) are situated on two longitudinal axes 16 running transversely to these storage compartments 3. To improve the stability of the storage unit 1, it preferably has a middle wall 18. The biopsy cassettes 8 to be inserted are provided with additional guidance by guide ribs 19. These guide ribs 19 preferably run perpendicular to the main footprint 2 and may alternately be situated on the middle wall 18, on the partitions 4, and on the peripheral frame 5. These guide ribs 19 preferably project perpendicular from their supporting wall into the storage compartments 3; those guide ribs 19 which taper toward the first and second openings 6, 7 and thus form an intake for the biopsy cassettes 8 to be inserted are especially preferred (not shown).

According to a second embodiment, the cushions 11 are implemented as single-sided, as shown in the storage compartments B1 through B12. In connection with the present invention, "single-sided" is to be understood to mean as "acting in one direction against the biopsy cassette which presses against them". These cushions 11 are implemented to engage using a frictional force on the vertical surfaces 13 of a biopsy cassette 8 inserted into a storage compartment 3 and are situated on a transverse axis 15 running centrally and longitudinally to this storage compartment 3.

As already shown in FIG. 1, the elements of cushions 11 and guide ribs 19 may be selected and/or combined with one another practically arbitrarily. The main footprint 2 of such a storage unit 1 preferably corresponds at least approximately to the SBS standard footprint of a standard microplate.

With the goal of a housing as many biopsy cassettes 8 as possible in the storage unit 1 shown in FIG. 1, two rows having storage compartments 3 each are situated standing substantially vertically in such a way that the biopsy cassettes 8, which stand on their faces 14a, 14b in relation to the main footprint 2, are situated transversely to the longitudinal direction of the storage unit 1. This results in a total of twenty-four cassettes 8 per storage unit 1 at the selected axial spacing of approximately 9 mm. If the peripheral frame 5 was narrowed, two additional cassettes could be housed in this storage unit 1; however, the position indicators would be significantly smaller or would have to be left out entirely.

As shown, the storage unit 1 has two beveled corners as orientation aids. These orientation aids may be partially or entirely dispensed with. Alternative orientation aids may be provided, for example, by a rounded corner or also by a corner equipped with a notch or a special relief (not shown). Attaching a bar code to an external surface of the peripheral frame and/or attaching a radiofrequency label, i.e., an "RFID tag", offers a further possibility. RFID tags, which not only have an individual, stored and retrievable identification code, but additionally comprise a writable and retrievable additional data memory are especially preferred. Attaching these RFID tags to locations on or in the storage unit 1 at which no mechanical action on these RFID tags is a concern is preferable. Barcodes are used alternatively or additionally to the RFID tags and are preferably provided in one-dimensional or two-dimensional form.

Figure 2:
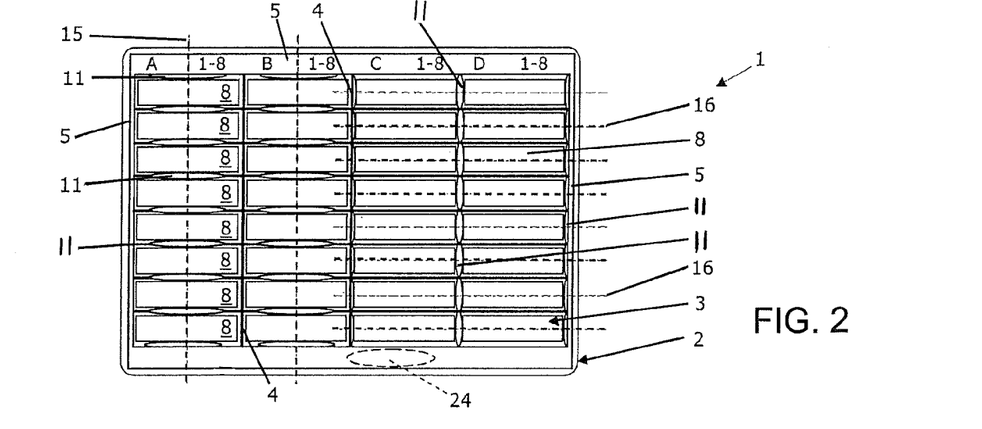
FIG. 2 shows a top view of a storage unit suitable for biopsy cassettes, in which the substantially vertically standing biopsy cassettes are packed tightly and situated longitudinally.

FIG. 2 shows a top view of a storage unit 1 for biological samples suitable for biopsy cassettes, in which the substantially vertically standing biopsy cassettes 8 are tightly packed and are situated longitudinally in relation to the longitudinal orientation of the storage unit 1. This storage unit 1 also comprises a main footprint 2 and multiple storage compartments 3, which are at least partially separated from one another by partitions 4 and are enclosed by a peripheral frame 5. The partitions 4 and the peripheral frame 5 are situated substantially perpendicular to the main footprint 2. In addition, these storage compartments 3 have both a first opening 6 and also a second opening 7 (see FIGS. 6 and 7). The storage compartments have the same, substantially rectangular cross-sectional profile over their entire height in the storage unit 1. The storage compartments 3 are fitted to the shape of a biopsy cassette 8, which is inserted either through the first opening 6 or the second opening 7 into these storage compartments 3 and stands on one of its faces 14a, 14b (see FIG. 5C). The storage compartments 3 additionally comprise retention means 9, which are implemented here as single-sided and double-sided cushions 11. The retention means 9 run substantially perpendicular to the main footprint 2 and are implemented to engage using frictional force on the support surfaces 12 (see FIG. 5A) or on the vertical surfaces 13 (see FIG. 5B) of a biopsy cassette 8 inserted into a storage compartment 3. These inserted biopsy cassettes 8 are prevented from falling out through the first opening 6 and/or the second opening 7 by this frictional force (no matter which side the storage unit 1 is tilted toward). The cushions 11 are also implemented as single-sided or double-sided here.

In the storage compartments A1, A8, B3 and B8, the cushions 11 are situated on the peripheral frame 5 and implemented to act single-sided. In the storage compartments A2 through A7 and B2 through B7, the cushions 11 are situated on the partitions 4 and implemented to act double-sided. In the storage compartments C1 through C8 and D1 through D8, the cushions 11 are situated on the peripheral frame 5 or on the partitions 4 and are implemented to act single-sided or double-sided accordingly. All of these cushions 11 are implemented to engage using frictional force on the support surfaces 12 or on the vertical surfaces 13 of a biopsy cassette 8 inserted into a storage compartment 3. Half of these (see storage compartments A1 through A8 and B1 through B8) are situated on a transverse axis 15 running centrally and transversely to these storage compartments 3. The other half (see storage compartments C1 through C8 and D1 through D8) is situated on a longitudinal axis 16 running centrally and longitudinally to these storage compartments 3.

As shown, all or a part of the middle walls may be formed by the cushions 11. In order to improve the stability of the storage unit 1, it may have a reinforced middle wall (not shown). Because of the tight space conditions existing here, which cause very precise positioning of the biopsy cassettes 8, guide ribs 19 are dispensed with here. With the goal of housing as many biopsy cassettes 8 as possible in the storage unit 1 shown in FIG. 2, four rows having eight storage compartments 3 each are situated in such a way that the biopsy cassettes 8, which stand on their faces 14a, 14b in relation to the main footprint 2, are situated longitudinally to the longitudinal direction of the storage unit 1. This results in a total of thirty-two cassettes 8 per storage unit 1 at the selected axial spacing of approximately 9 mm. If the peripheral frame 5 was narrowed, four additional cassettes could be housed in this storage unit 1; however, the position indicators would then be significantly smaller or would have to be left out entirely.

Figure 3:
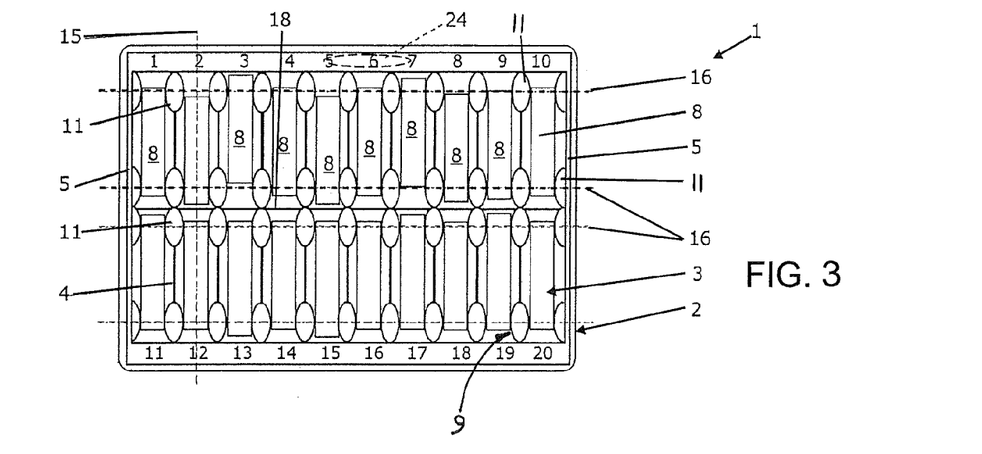
FIG. 3 shows a first top view of a storage unit suitable for biopsy cassettes, in which the substantially vertically standing biopsy cassettes are packed loosely and situated transversely.

FIG. 3 shows a first top view of a storage unit 1 suitable for biopsy cassettes, in which the substantially vertically standing biopsy cassettes 8 are loosely packed and situated transversely. In contrast to the two storage units 1 described above, the number of the insertable biopsy cassettes 8 is reduced to a total of twenty and cushions 11 having a larger volume are used. In addition, guide ribs 19 were dispensed with. The storage unit 1 also comprises a main footprint 2 and multiple storage compartments 3 here, which are at least partially separated from one another by partitions 4 and are enclosed by a peripheral frame 5. The partitions 4 and the peripheral frame 5 are also situated substantially perpendicular to the main footprint 2. In addition, the storage compartments 3 have both a first opening 6 and also a second opening 7 (see FIGS. 6 and 7). The storage compartments 3 have the same, substantially rectangular cross-sectional profile over their entire height in the storage unit 1 here, The storage compartments 3 are fitted to the shape of a biopsy cassette 8, which has been inserted either through the first opening 6 or the second opening 7 into these storage compartments 3 and stands on one of its faces 14a, 14b (see FIG. 5C).

The purpose of this embodiment is to provide those storage compartments 3, which leave greater play for the dimensions of the biopsy cassettes 8 to be inserted. In addition, this embodiment of the storage unit 1 allows quite imprecise insertion of the biopsy cassettes 8, but nonetheless ensures these biopsy cassettes 8 are held securely in the storage compartments 3. In order to improve the stability of the storage unit 1, it may have a reinforced middle wall 18 (not shown).

The single-sided acting cushions 11 are situated on the peripheral frame 5 in the storage compartments 1, 10, 11, and 20, All double-sided acting cushions 11 are situated in the area of the partitions. All of these cushions 11 are implemented to engage using frictional force on the support surfaces 12 of a biopsy cassette 8 inserted into a storage compartment 3 and are situated in a row of storage compartments (see 1 through 10 and 11 through 20) on two longitudinal axes 16 running transversely to these storage compartments 3.

Figure 4:
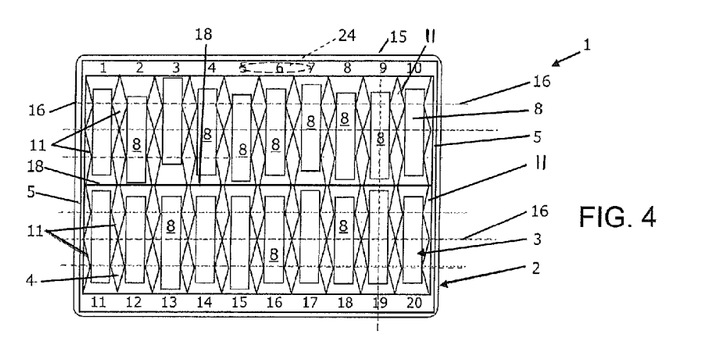
FIG. 4 shows a second top view of a storage unit suitable for biopsy cassettes, in which the substantially vertically standing biopsy cassettes are packed loosely and situated transversely.

FIG. 4 shows a second top view of a storage unit 1 suitable for biopsy cassettes, in which the substantially vertically standing biopsy cassettes 8 are loosely packed and situated transversely. In contrast to FIG. 3, the cushions 11 are implemented as rhomboidal in cross-section and not elliptical In addition, the most pronounced points of the cushions are placed so that they are at a distance of approximately a fourth of the length of a storage compartment 3 from the peripheral frame 5 or the middle wall 18. This configuration in turn allows storage compartments 3 to be provided which allow greater play for the dimensions of the biopsy cassettes 8 to be inserted. In addition, this embodiment of the storage unit 1 also allows quite imprecise insertion of the biopsy cassettes 8, but nonetheless ensures that these biopsy cassettes 8 are held securely in the storage compartments 3. In order to improve the stability of the storage unit 1, it may have a reinforced middle wall 18 (not shown). The partitions 4 are replaced entirely by the cushions 11 here, which provide a larger spring path for the cushions.

Because the embodiments of the storage compartments 3 shown in FIG. 3 and FIG. 4 include a larger space around the inserted biopsy cassettes 8, storage units 1 of this type are especially well suitable for storing the biopsy cassettes 8 at low (−80° C.) or very low temperatures (−196° C.). This larger space improves the gas exchange in the immediate surroundings of a cassette, so that it is well reachable and optimally cooled by the $CO_2$ cooling gas or the liquid nitrogen. The single-sided or double-sided cushions 11 preferably extend at the same effective cross-section over substantially the entire height of the storage compartments 3 and are preferably implemented as open in the area of the first opening 6 and the second opening 7. These cushions may additionally have passages or be implemented as net-like (not shown).

FIG. 5 shows views of a closed biopsy cassette, known per se from the prior art, made of injection-molded plastic, such as polypropylene. The interior of such a cassette typically measures approximately 30×25×5 mm, FIG. 5A shows a top view of the support surface 12 of the cover 27 of the biopsy cassette 8. The cover 27 has multiple slots 33, of which only a part are shown. The cover 27 is connected via the hinge 29 to the cage 28, of which the beveled face 14a is well visible on the right side. A tab 34 shaped onto the cover makes it easier to open the cassette by hand. In the corners of the biopsy cassette 8 not occupied by the tab, pins 35 are located, which define a shared level together with the tab 34.

FIG. 5B shows a view of a vertical surface 13 of the cage 28 of the biopsy cassette 8. The hinge 29 and a pin 35 are shown on the left side. The tab 34 and the beveled front face 14a are indicated on the right side. The curve of the floor 36 of the cassette 8 is drawn using dashed lines.

FIG. 5C shows a view of the beveled front face 14a of the cage 28 of the biopsy cassette 8. The tab 34 and a pin 35 are visible in the area of the cover 27. A two-dimensional bar code is printed on the right side. The course of the floor 36, which comprises a similar slotted pattern as the cover 27 of the cassette (not shown), is drawn using dashed lines.

FIG. 6 shows a vertical section through two storage units situated one above the other in alignment, having a main footprint 2 corresponding to the SBS standard footprint of a standard microplate, a biopsy cassette 8 being pushed at least substantially vertically by a manipulator 23a from the upper storage unit into the lower storage unit (toward the main footprint 2) precisely at this instant. The manipulator 23a is part of the device 22 of a transfer system 21, using which at least two storage units 1 may be situated one above the other in alignment and displaced in relation to one another. The storage units 1 shown are located in a mutual position, in which all storage compartments 3 corresponding to one another of these two storage units 1 are placed precisely one above another. At least one of these two storage units 1 may be displaced in relation to the other using the device 22 in such a way that any arbitrary storage compartment 3 of the upper storage unit 1 may be assigned to an arbitrary storage compartment 3 of the lower storage unit 1 standing exactly in alignment in relation to one another. It is then easy to insert, preferably, a robotic manipulator 23a into a specific and individually selected storage compartment 3 and push the biopsy cassette 8 located therein into a previously assigned storage compartment 3 of a second storage unit 1 (toward the main footprint 2). The sliding resistance caused by the frictional force between the retention means 9 and the biopsy cassette 8 to be displaced causes this biopsy cassette not to fall out after it is transferred from the upper storage unit 1 into the lower storage unit 1. The manipulator 23a is preferably fitted to the shape of the front, beveled face 14a of the biopsy cassette 8 and may have a friction-increasing coating, which prevents slipping on the beveled face 14a of the biopsy cassette 8.

As shown, the biopsy cassette 8 are preferably inserted substantially vertically into the storage compartments 3 of a storage unit 1 in such a way that the front, beveled faces 14a of the biopsy cassettes 8 are on top and may be read from this direction by eye or automatically using an appropriate reading device. An RFID tag is preferably housed in the dead-end space 37 on the bottom of the biopsy cassette 8 (see FIG. 5B).

Alternative to the pushing direction shown of the manipulator 23a, it may also run in the opposite direction, i.e., from bottom to top (not shown). Notwithstanding the illustration in FIG. 6, the bottom storage unit may have a closed floor (not shown) and solely be used as a collection unit for biopsy cassettes 8. Therefore, the use of at least one storage unit 1 for biopsy cassettes 8 suffices to perform the alternative method, in which selected biopsy cassettes 8 are transferred from one storage unit 1 or multiple such storage units to a collection unit for biopsy cassettes 8.

FIG. 7 shows a vertical section through two storage units 1 with one above the other in alignment having a main footprint 2 deviating from the SBS standard footprint of a standard microplate, a biopsy cassette 8 being pushed at least substantially horizontally by a manipulator 23b from the lower storage unit into the upper storage unit (away from the main footprint 2) precisely at this instant. The two storage units 1 stand on a secondary footprint 20, which is oriented substantially perpendicular to the main footprint 2. Notwithstanding the illustration selected here, these two storage units 1 may have a secondary footprint 20 and a main footprint 2 corresponding to the SBS standard footprint of a standard microplate.

The manipulator 23b is part of the device 22 of a transfer system 21, in which at least two storage units 1 are situated one above the other in alignment and may be displaced relative to one another. The storage units 1 shown are located in a mutual position, by which only a part and non-corresponding storage compartments 3 of these two storage units 1 are placed precisely one above the other. At least one of these two storage units 1 was displaced relative to the other using the device 22 in such a way that any arbitrary storage compartment 3 of the upper storage unit 1 is assigned to an arbitrary storage compartment 3 of the lower storage unit 1 standing exactly in alignment one over the other. Preferably, a robotic manipulator 23b is inserted into a specific and individually selected storage compartment 3 and the biopsy cassette 8 located therein is pushed into a previously assigned storage compartment 3 of the other storage unit 1 (away from the main footprint 2). The sliding resistance caused by the frictional force between the retention means 9 and the biopsy cassette 8 to be displaced prevents this biopsy cassette from falling out after it is transferred from the lower storage unit 1 into the upper storage unit 1. The manipulator 23b is preferably fitted to the shape of the rear, non-beveled face 14b of the biopsy cassette 8 and may have a friction-increasing coating, which prevents slipping on this face 14b of the biopsy cassette 8.

As shown, the biopsy cassettes 8 are preferably inserted here into the storage compartments 3 of a storage unit 1 in such a way that the front, beveled faces 14a of the biopsy cassettes 8 are in front (away from the main footprint 2) and may be read from this direction by eye or automatically using a corresponding read device. An RFID tag is preferably housed in the dead-end space 37 on the bottom of the biopsy cassette 8 (see FIG. 5B).

As an alternative to the pushing direction shown of the manipulator 23b, it may also run in the opposite direction, i.e., from front to rear (i.e., from left to right, not shown). Notwithstanding the illustration in FIG. 7, the upper storage unit may have a closed floor (not shown) and solely be used as a collection unit for biopsy cassettes 8.

Figure 8:
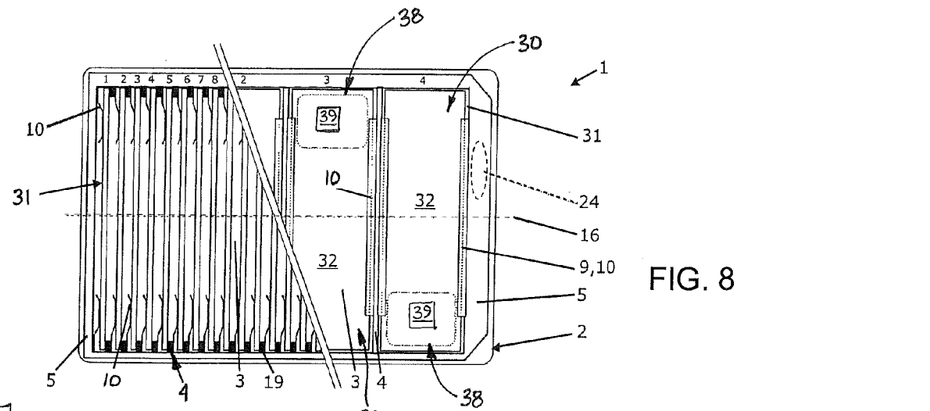
FIG. 8 shows a top view of a storage unit suitable for glass slides, in which the glass slides are situated transversely and standing substantially vertically, tightly packed or transversely and lying.

FIG. 8 shows a top view of a storage unit 1 suitable for glass slides, in which the glass slides 30 are tightly packed transversely and standing substantially vertically (left side FIG. 8) or transversely and lying (right side FIG. 8). In these configurations, it is unimportant in principle how the surface of the object carrier, to which the samples, i.e., for example, the tissue sections (e.g., from pathology), cell smears (e.g., blood smears), or cell layers (e.g., from a cell culture) are located, stands or lies. In any case, it is ensured that the sample regions of the glass slides 30 are not mechanically strained.

This storage unit 1 for biological samples has a substantially horizontal main footprint 2 and multiple storage compartments 3, which are at least partially separated from one another by partitions 4 and are enclosed by a peripheral frame 5. The partitions 4 and the peripheral frame 5 are situated substantially perpendicular to the main footprint 2. In addition, these storage compartments 3 have both a first opening 6 and also a second opening 7. The storage compartments 3 are fitted to the shape of a glass slide 30 and comprise retention means 9 which prevent the glass slides 30 inserted through the first opening 6 and/or the second opening 7 into the storage compartments 3 from falling out through the first opening 6 and/or the second opening 7. The storage compartments 3 preferably have a substantially rectangular cross-section and are implemented to each receive one glass slide 30 for biological samples either standing on a longitudinal edge 31 or lying on a surface 32 in relation to the main footprint 2.

The retention means 9 are preferably selected from a group which comprises single-sided and double-sided ribs 10. In connection with the present invention, "single-sided" is to be understood to mean "acting against a slide which presses against it". In connection with the present invention, "double-sided" is to be understood to mean "acting against two slides which press against it". The retention means 9 (ribs 10 here) run either substantially perpendicular to the main footprint 2 (see left side of FIG. 8) or substantially parallel to the main footprint 2 (see right side of FIG. 8).

The ribs 10 situated substantially perpendicular to the main footprint 2 are implemented to engage using frictional force on the surface 32 of a glass slide 30 inserted substantially vertically into a storage compartment 3. This inserted glass slide 30 is prevented from falling out through the first opening 6 and/or the second opening 7 (no matter which side the storage unit 1 is tilted toward) by this frictional force. These ribs 10 begin at the peripheral frame 5 (not shown) or at its guide ribs which extend perpendicular to the main footprint 2. These guide ribs 19 assume the function of the partitions 4 and thus at least partially separate the storage compartments 3 from one another. The ribs 10 preferably have a width such that they do not reach the sample areas of the glass slides 30. The ribs 10 engage the glass slides 30 and press them elastically against the guide ribs 19, so that the glass slides 30 are held securely in their storage compartments 3. The dense packing of the storage compartments 3 allows up to twenty-four or more glass slides 30, which preferably stand substantially vertically on a longitudinal edge 31, to be situated in a single storage unit 1.

The ribs 10 situated substantially parallel to the main footprint 2 are implemented to rest partially on the surface 32 of a glass slide 30 inserted into the storage compartment 3. These inserted glass slides 30 are prevented from falling out through the first opening 6 and/or the second opening 7 (no matter which side the storage unit 1 is tilted toward) by this partial contact. The ribs 10 are shaped onto the top and bottom of the partitions 4 here or attached thereto (e.g., by welding or gluing, not shown) and project on both sides beyond these partitions 4 (see FIG. 10). The upper and lower ribs 10 situated on the peripheral frame 5 are preferably at the same height as the corresponding ribs attached to the partitions 4. However, the ribs 10 are preferably implemented as only wide enough that they do not reach the sample areas of the glass slide 30. The ribs 10 may be implemented in one piece and extend over a partial length of the storage compartment 3 (see FIG. 8, right side); however, they may also be divided (not shown). In an alternative configuration, the ribs 10 are situated on the transverse sides of the storage compartments 3 (not shown). Combinations of the configurations shown and alternative configurations are also provided. The horizontal configuration allows the storage of up to 4 glass slides 30 in a storage unit 1.

Figure 9:
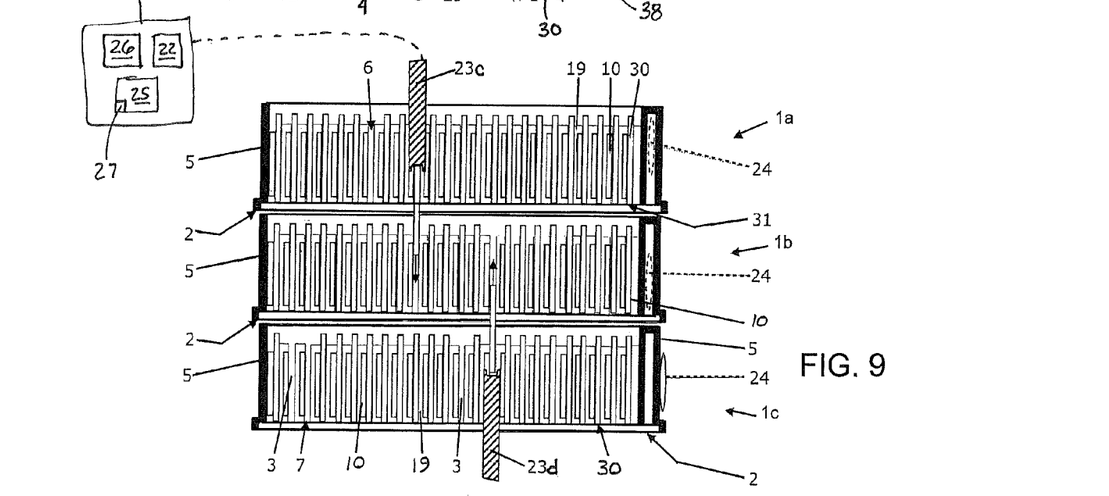
FIG. 9 shows a vertical section through three storage units situated one above the other in alignment having the SBS standard footprint of a standard microplate, a standing glass slide being pushed vertically from the upper storage unit into the middle storage unit and from the lower storage unit into the middle storage unit.

FIG. 9 shows a vertical section through three storage units 1a, 1b and 1c situated one on top of another in alignment having a main footprint 2 corresponding to the SBS standard footprint of a standard microplate. A single substantially vertical glass slide 30 is pushed by a first manipulator 23c vertically from the upper storage unit 1*a* into the middle storage unit 1*b* (toward the main footprint 2) and one glass slide is pushed by a second manipulator 23*d* from the lower storage unit 1*c* into the middle storage unit 1*a* (away from the main footprint 2) precisely at this point.

The manipulator 23*c*, 23*d* is part of the device 22 of a transfer system 21, using which at least two storage units 1 may be situated one above the other in alignment and displaced in relation to one another. The storage units 1 shown are located in a mutual position in which all storage compartments 3 of these two storage units 1 corresponding to one another are placed precisely one above another. At least one of these two storage units 1 may be displaced in relation to the other using the device 22 in such a way that any arbitrary storage compartment 3 of the upper storage unit 1 may be assigned standing in alignment directly in relation to another an arbitrary storage compartment of the lower storage unit 1. It is then easy to insert, preferably, a robotic manipulator 23*c*, 23*d* into a specific and individually selected storage compartment 3 and to push the glass slide 30 located therein into a previously assigned storage compartment 3 of a second storage unit 1 (e.g., toward the main footprint 2). The sliding resistance caused by the frictional force between the retention means 9 and the glass slide 30 prevents glass slide 30 from falling out after it is transferred from the upper storage unit 1 into the lower storage unit 1. The manipulator 23*c*, 23*d* is preferably fitted to the shape of the substantially vertically standing glass slide 30 and may additionally have a friction-reinforcing coating, which prevents slipping on the longitudinal edge 31 of the glass slide 30.

As shown in FIG. 9, the glass slides 30 are preferably inserted standing substantially vertically on a longitudinal edge 31 into the storage compartments 3 of a storage unit 1 in such a way that they are spaced (if minimal) from one another. Identifiers 24 (e.g., in the form of barcode markings) are preferably attached along the upper longitudinal edge 31 and/or in the area proximal to these longitudinal edges of grip areas 38 situated on the narrow sides (see also FIG. 8), so that these may be read by eye or automatically using a corresponding read device. An RFID tag 39 is preferably attached in a grip area 38 of the glass slide 30 (see FIG. 8).

As an alternative to the first pushing direction of the manipulator 23*c*, 23*d*, it may also run in the opposite direction, i.e., from bottom to top. Notwithstanding the illustration in FIG. 9, only one storage unit 1 and a collection unit may also be used, the collection unit being able to lie on the top or bottom, having a closed floor (not shown) on the side distal from the storage unit 1, and solely being used as a collection unit for glass slides 30. Therefore, the use of at least one storage unit 1 for glass slides 30 suffices to perform the alternative method, in which selected glass slides 30 are transferred from one storage unit 1 or multiple such storage units to a collection unit for glass slides 30.

Notwithstanding FIG. 9 and corresponding to the configurations shown in FIG. 7, two storage units 1 situated one above the other in alignment may additionally or alternatively be equipped with a main footprint 2 deviating from the SBS standard footprint of a standard microplate. These alternative storage units 1 stand on this secondary footprint 20, which is oriented substantially perpendicular to the main footprint 2. Preferably, a robotic manipulator is inserted into a specific and individually selected storage compartment 3 and pushes the glass slide 30 located therein into a previously assigned storage compartment 3 of the other storage unit 1 (away from the main footprint 2). The sliding resistance caused by the frictional force between the retention means 9 and the glass slide 30 to be displaced prevents this glass slide 30 from falling out of this storage unit 1 after it is transferred. As an alternative to the indicated pushing direction of the manipulator, it may also run in the opposite direction, i.e., from left to right (not shown). The upper storage unit may also have a closed floor or cover (not shown) and may solely be used as a collection unit for glass slides 30.

Figure 10:
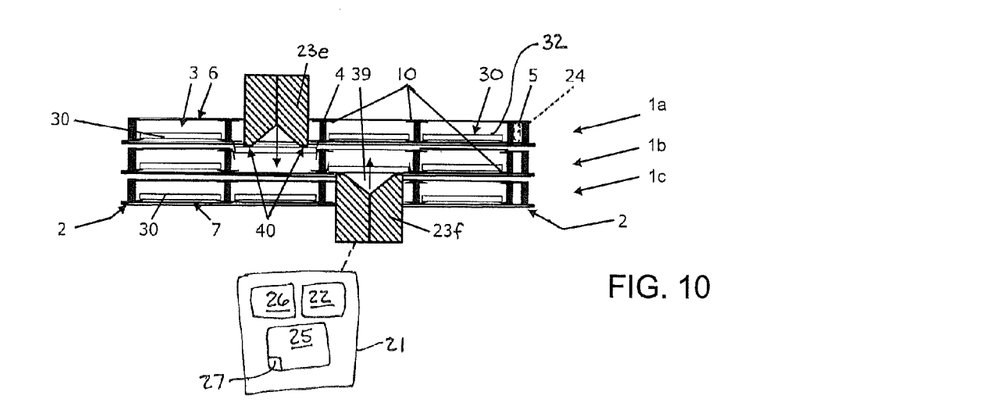
FIG. 10 shows a vertical section through three storage units situated one above the other in alignment having the SBS standard footprint of a standard microplate, a lying glass slide being pushed vertically from the upper storage unit into the middle storage unit and from the lower storage unit into the middle storage unit.

FIG. 10 shows a vertical section through three storage units 1*a*, 1*b* and 1*c*, situated one above another in alignment, having a main footprint 2 corresponding to the SBS standard footprint of a standard microplate. As illustrated, one horizontally-lying glass slide 30 is pushed by a first manipulator 23*e* vertically from the upper storage unit 1*a* into the middle storage unit 1*b* (toward the main footprint 2) and one glass slide is pushed by a second manipulator 23*f* from the lower storage unit 1*c* vertically into the middle storage unit 1*b* (away from the main footprint 2). During the transfer pushing of the substantially horizontal slide 30, it is pressed against the closest ribs 10 of the storage unit 1*b*, in which the slide 30 initially lies. These ribs 10 may be those which constrict the first, upper opening 6 of the original storage compartment 3. These ribs 10 may, however, also be those on which the slide 30 rests and which constrict the second, lower opening 7 of the original storage compartment 3. During the further movement of the slide 30, these ribs are elastically deformed by the slide 30, so that the ribs 10 yield elastically with deformation and temporarily engage the two longitudinal edges (see FIG. 9) with a frictional force, for example. The slide 30 is pushed further by the manipulator 23*e*, 23*f* against this sliding resistance, the ribs 10 delimiting the storage compartment 3 of the next storage unit 1 also elastically yielding and temporarily engaging the slide 30 with a frictional force. If the slide 30 is conveyed from top to bottom, it falls on the supporting ribs 10 of the new storage unit 1 as soon as it has left the influence range of the ribs just deformed. If the slide 30 is conveyed from bottom to top, it is moved further nearly up to the ribs 10 constricting the new storage compartment 3 on top. The slide 30 thus leaves the influence range of the ribs just deformed, which immediately spring back into their substantially vertical original position. The manipulator 23*f* may now be lowered and the slide 30 conveyed from bottom to top remains lying on the ribs 10 of the new storage unit 1 which support it.

It results from this description that the transferred slide 30 is moved over at least a part of its transfer path from one storage unit 1 to the other against the sliding resistance of ribs 10. This sliding resistance allows careful depositing of a slide 30 pushed from top to bottom in particular. The manipulator 23*e*, 23*f* has recesses 39, thanks to which the samples on the slide 30 are not strained. The manipulator 23*e*, 23*f* may have a coating on its pushing faces 40 to increase the sliding resistance of the slide 30 and/or to softly and elastically engage the slide 30.

A preferred transfer system for transferring biopsy cassettes 8 or slides 30 from one storage unit 1 to a second storage unit 1 or to a collection unit preferably comprises a device 22, using which at least two storage units 1 or at least one storage unit 1 and one collection unit may be situated one above the other in alignment and displaced in relation to one another. Such a transfer system 21 preferably additionally comprises a manipulator 23*a*-23*f*, using which a biopsy cassette 8 inserted into an individual storage compartment 3 or a glass slide 30 inserted into an individual storage compartment 3 may be pushed from one storage unit 1 into the other storage unit 1 or into the collection unit.

In a first preferred transfer system, the device 22 is implemented for situating the at least two storage units 1 or at least one storage unit 1 and one collection unit in substantially horizontal planes which lie one above the other. In addition, the manipulator 23a-23f is implemented for substantially vertically pushing a biopsy cassette 8 or a glass slide 30 toward the main footprint 2 or away therefrom.

In a second preferred transfer system 21, the device 22 is implemented for situating the at least two storage units 1 or at least one storage unit 1 and one collection unit in substantially vertical planes which lie one above the other and this manipulator 23a-23f implemented for substantially horizontally pushing a biopsy cassettes 8 or a glass slide 30 toward the main footprint 2 or away therefrom.

Such transfer systems 21 preferably additionally comprise a warehouse unit 25 for storing multiple storage units 1 according to one of claims 1 through 15 and a robot 26, using which such storage units 1 may be removed from the warehouse unit 25 and/or stored in this warehouse unit 25. Warehouse units 25 which comprise an array of retainers 27 having bearing surfaces 17 are especially preferred, the bearing surfaces 17 of these retainers 27 being implemented to be engaged by the main footprint 2 or a secondary footprint 20 of a storage unit 1.

The storage units 1 according to the present invention and the biopsy cassettes 8 or glass slides 30 comprise at least one identifier 24, which is selected from RFID tags and barcodes, for unique identification and tracking, The storage units 1 according to the present invention are preferably produced in the injection molding method and comprise a polymer or multiple polymers, which preferably include polycarbonate (PC).

The use of biopsy cassettes 8 or glass slides 30 situated in individual storage compartments 3 of storage units 1 according to the present invention for biological samples has the purpose of storing and providing a large number of such biological samples. Each storage unit 1 comprises a main footprint 2 and multiple storage compartments 3, which are at least partially separated from one another by partitions 4 and are enclosed by a peripheral frame 5. In addition, the partitions 4 and the peripheral frame 5 are situated substantially perpendicular to the main footprint 2 and these storage compartments 3 have both a first opening 6 and also a second opening 7. The storage compartments 3 according to the present invention are fitted to the shape of biopsy cassettes 8 or glass slides 30. This use provides that each biopsy cassette & or each glass slide 30 is inserted through the first opening 6 or the second opening 7 into a storage compartment 3, which has retention means 9 which prevent the inserted biopsy cassettes 8 or the inserted glass slide 30 from falling out through the first opening 6 and/or the second opening 7.

For the robotic handling and warehousing of these storage units 1, they preferably have a main footprint 2, which at least approximately corresponds to the SBS standard footprint of a standard microplate. One or more of these biopsy cassettes 8 or glass slides 30 may be removed robotically and automatically from the corresponding storage compartments 3 of a first storage unit 1 and inserted into selected storage compartments 3 of a second storage unit 1 or a collection unit. Preferably, two of these storage units 1 are situated one above the other in alignment and displaced in relation to one another using a device 22 of a transfer system 21, biopsy cassettes 8 or glass slides 30 being pushed, vertically from the upper storage unit 1 into the storage unit 1 or collection unit lying underneath using a manipulator 23 of this transfer system 21.

Combinations and variations of the ribs 10, cushions 11, and guide ribs 19 shown and/or described are included in the scope of the present invention.

The invention claimed is:

1. A storage unit for storing biological samples fixed on cassettes or slides, the storage unit comprising:
   a frame;
   a plurality of storage compartments disposed within the frame configured to hold biological sample slides or biological sample cassettes, each storage compartment at least partially separated from other storage compartments by partitions and having an upper opening and a bottom opening, each storage compartment fitted to the shape of a cassette or slide, wherein the upper opening is dimensioned to pass a cassette or slide therethrough; and
   retention means extending partially into the upper opening, the retention means adapted to prevent the cassette or slide inserted within the storage compartment from falling out of the upper opening, wherein the retention means is further adapted to elastically yield when a cassette or slide is pressed against the retention means to insert the cassette or slide into the storage compartment;
   wherein the bottom opening, bounded by a bottom-most surface of the storage compartment, is configured so that the bottom opening allows insertion of a manipulator through the bottom opening into the storage compartment and engagement with the cassette or slide in the storage compartment causing displacement of the cassette or slide therein, and the retention means and the bottom opening are arranged so that upward displacement from the bottom opening towards the upper opening, of the cassette or slide from a seated position in a respective storage compartment, caused by the manipulator alone through the bottom opening independently releases the cassette or slide from the retention means engaging the cassette or slide in the seated position.

2. The storage unit of claim 1, wherein the frame has dimensions adapted to fit within a footprint of a microplate.

3. The storage unit of claim 2, wherein the footprint is a standard SBS footprint.

4. The storage unit of claim 2, wherein the storage compartment is configured to retain the cassette or slide in a vertical orientation relative to the footprint.

5. The storage unit of claim 2, wherein the storage compartment is configured to retain the cassette or slide in a horizontal orientation relative to the footprint.

6. The storage unit of claim 1, wherein the retention means comprises single-sided or double-sided ribs.

7. The storage unit of claim 1, wherein the retention means comprises single-sided or double-sided cushions.

8. The storage unit of claim 1, wherein the retention means extends partially into each of the upper opening and the bottom opening.

9. The storage unit of claim 8, wherein the bottom opening is dimensioned for insertion of the manipulator to push a selected cassette or slide through the upper opening.

10. The storage unit of claim 9, wherein the storage unit is adapted to be situated in a vertical arrangement with other storage units, and wherein the manipulator is adapted to transfer a selected cassette or slide from the storage compartment of one of a lower storage unit and an upper storage unit to a selected storage compartment of the other of the upper storage unit and the lower storage unit when the storage compartments are aligned.

11. The storage unit of claim 10, wherein the frames of each of the upper storage unit and the lower storage unit are displaced relative to each other.

12. The storage unit of claim 10, wherein the frames of each of the upper storage unit and the lower storage unit are aligned with each other.

13. The storage unit of claim 8, wherein the upper opening is dimensioned for insertion of the manipulator to push a selected cassette or slide through the bottom opening.

14. The storage unit of claim 13, wherein the storage unit is adapted to be situated in a vertical arrangement with other storage units, and wherein the manipulator is adapted to transfer a selected cassette or slide from the storage compartment of one of an upper storage unit and a lower storage unit to a selected storage compartment of the other of the lower storage unit and the upper storage unit when the storage compartments are aligned.

15. The storage unit of claim 14, wherein the frames of each of the upper storage unit and the lower storage unit are displaced relative to each other.

16. The storage unit of claim 14, wherein the frames of each of the upper storage unit and the lower storage unit are aligned with each other.

17. A storage unit in an automated storage and transfer system for handling and storing biological samples fixed on cassettes or slides, the storage unit comprising:
  a frame having dimensions that match a microplate footprint;
  a plurality of storage compartments disposed within the frame configured to hold biological sample slides or biological sample cassettes, each storage compartment at least partially separated from other storage compartments by vertical partitions and having an upper opening and a bottom opening, each storage compartment fitted to the shape of a cassette or slide, wherein the upper opening is dimensioned to pass a cassette or slide therethrough and to permit insertion of a robotic manipulator adapted for inserting cassettes or slides into and removing cassettes or slides from a selected storage compartment; and
  retention means extending partially into the upper opening, the retention means adapted to prevent the cassette or slide inserted within the storage compartment from falling out of the upper opening, wherein the retention means is further adapted to elastically yield when a cassette or slide is pressed against the retention means to insert the cassette or slide into the storage compartment;
  wherein the bottom opening, bounded by a bottom-most surface of the storage compartment, is configured so that the bottom opening allows insertion of the robotic manipulator through the bottom opening into the storage compartment and engagement with the cassette or slide in the storage compartment causing displacement of the cassette or slide therein, and the retention means and the bottom opening are arranged so that upward displacement from the bottom opening towards the upper opening, of the biological sample slides or biological sample cassettes from a seated position in a respective storage compartment, caused by the robotic manipulator alone through the bottom opening independently releases the biological sample cassettes or biological sample slides from the retention means engaging the biological sample cassettes or biological sample slides in the seated position.

18. The storage unit of claim 17, wherein the microplate footprint is a standard SBS footprint.

19. The storage unit of claim 17, wherein the retention means further applies a frictional force against the cassette or slide to generate a temporary sliding resistance to a force applied by the robotic manipulator.

20. The storage unit of claim 17, wherein the storage compartment is configured to retain the cassette or slide in a vertical orientation relative to the footprint.

21. The storage unit of claim 17, wherein the storage compartment is configured to retain the cassette or slide in a horizontal orientation relative to the footprint.

22. The storage unit of claim 17, wherein the retention means extends partially into each of the upper opening and the bottom opening.

23. The storage unit of claim 22, wherein the storage unit is adapted to be situated in a vertical arrangement with other storage units so that the storage compartments of each storage unit are oriented in the same orientation relative to the footprint, and wherein the robotic manipulator is adapted to transfer a selected cassette or slide from the storage compartment of a first storage unit in the vertical arrangement to a selected storage compartment of a second storage unit in the vertical arrangement when the storage compartments are aligned.

24. The storage unit of claim 23, wherein the frame of the first storage unit and the frame of the second storage unit are displaced relative to each other.

25. The storage unit of claim 23, wherein the frame of the first storage unit and the frame of the second storage unit are aligned with each other.

26. A storage unit for storing biological samples on cassettes or slides, the storage unit comprising:
  a frame;
  a plurality of storage compartments disposed within the frame, each storage compartment at least partially separated from other storage compartments by partitions and having an upper opening and a bottom opening, each storage compartment fitted to the shape of a cassette or slide, wherein the upper opening is dimensioned to pass a cassette or slide therethrough; and
  a retainer extending partially into the storage compartment, the retainer adapted to hold the cassette or slide within the storage compartment, wherein the retainer is further adapted to yield when a cassette or slide is pressed against the retainer when inserting the cassette or slide into the storage compartment;
  wherein the bottom opening, bounded by a bottom-most surface of the storage compartment, is configured so that the bottom opening allows insertion of a manipulator through the bottom opening into the storage compartment and engagement with the cassette or slide in the storage compartment causing displacement of the cassette or slide therein, and the retention means and the bottom opening are arranged so that upward displacement from the bottom opening towards the upper opening, of the cassette or slide from a seated position in a respective storage compartment, caused by the manipulator alone through the bottom opening independently releases the cassette or slide from the retention means engaging the cassette or slide in the seated position.

27. A storage unit in an automated storage and transfer system for handling and storing biological samples on cassettes or slides, the storage unit comprising:
  a frame having dimensions that match a microplate footprint;
  a plurality of storage compartments disposed within the frame, each storage compartment at least partially separated from other storage compartments by vertical partitions and having an upper opening and a bottom opening, each storage compartment fitted to the shape of a cassette or slide, wherein the upper opening is dimensioned to pass a cassette or slide therethrough and to permit insertion of a robotic manipulator adapted for inserting cassettes or slides into and removing cassettes or slides from a selected storage compartment; and
  a retainer extending partially into the storage compartment, the retainer adapted to hold the cassette or slide within the storage compartment, wherein the retainer is further adapted to yield when a cassette or slide is pressed against the retainer when inserting the cassette or slide into the storage compartment;

wherein the bottom opening, bounded by a bottom-most surface of the storage compartment, is configured so that the bottom opening allows insertion of the robotic manipulator through the bottom opening into the storage compartment and engagement with the cassette or slide in the storage compartment causing displacement of the cassette or slide therein, and the retention means and the bottom opening are arranged so that upward displacement from the bottom opening towards the upper opening, of the cassette or slide from a seated position in a respective storage compartment, caused by the robotic manipulator alone through the bottom opening independently releases the cassette or slide from the retention means engaging the cassette or slide in the seated position.

\* \* \* \* \*